(12) United States Patent
Obrigkeit et al.

(10) Patent No.: US 9,452,061 B2
(45) Date of Patent: Sep. 27, 2016

(54) SPINAL FUSION CAGE

(75) Inventors: Darren Donald Obrigkeit, Aachen (DE); Jacob Koenen, Ah Sittard (NL); Detlef Olaf Alexander Schumann, Aachen (DE); Leo Smit, Ae Orisbeek (NL)

(73) Assignee: DSM IP ASSETS B.V., Heerlen (NL)

( * ) Notice: Subject to any disclaimer, the term of this patent is extended or adjusted under 35 U.S.C. 154(b) by 174 days.

(21) Appl. No.: 13/203,131

(22) PCT Filed: Mar. 5, 2010

(86) PCT No.: PCT/EP2010/052854
§ 371 (c)(1),
(2), (4) Date: Nov. 7, 2011

(87) PCT Pub. No.: WO2010/100267
PCT Pub. Date: Sep. 10, 2010

(65) Prior Publication Data
US 2012/0046750 A1   Feb. 23, 2012

(30) Foreign Application Priority Data

Mar. 5, 2009  (EP) .................. PCT/EP2009/052643
Sep. 4, 2009  (EP) ..................................... 09169519

(51) Int. Cl.
| A61F 2/44 | (2006.01) |
| A61L 27/18 | (2006.01) |
| A61L 27/56 | (2006.01) |
| A61B 17/86 | (2006.01) |
| A61F 2/30 | (2006.01) |

(52) U.S. Cl.
CPC .............. *A61F 2/4455* (2013.01); *A61L 27/18* (2013.01); *A61L 27/56* (2013.01); *A61B 17/86* (2013.01); *A61F 2002/30014* (2013.01); *A61F 2002/30016* (2013.01); *A61F 2002/3097* (2013.01); *A61F 2002/30448* (2013.01); *A61F 2220/005* (2013.01); *A61F 2250/0018* (2013.01); *A61F 2250/0019* (2013.01); *A61F 2310/00017* (2013.01); *A61F 2310/00023* (2013.01); *A61F 2310/00029* (2013.01)

(58) Field of Classification Search
CPC ...... A61F 2/442; A61F 2/4455; A61F 2/446; A61F 2/4465; A61F 2/447; A61F 2002/30003; A61F 2002/30004; A61F 2002/30006; A61F 2002/30014; A61F 2002/30016; A61F 2002/30018; A61F 2002/30069; A61F 2002/443; A61F 2002/30563; A61F 2002/30604; A61F 2250/0018; A61F 2002/30971
USPC ........................................... 623/17.11–17.16
See application file for complete search history.

(56) References Cited

U.S. PATENT DOCUMENTS

| 4,739,013 | A | | 4/1988 | Pinchuk | |
|---|---|---|---|---|---|
| 4,810,749 | A | | 3/1989 | Pinchuk | |
| 4,863,477 | A | * | 9/1989 | Monson | A61F 2/441 623/17.12 |
| 5,035,716 | A | * | 7/1991 | Downey | A61F 2/442 623/17.16 |
| 5,071,437 | A | * | 12/1991 | Steffee | A61F 2/442 606/247 |
| 5,133,742 | A | | 7/1992 | Pinchuk | |
| 5,229,431 | A | | 7/1993 | Pinchuk | |
| 5,320,644 | A | * | 6/1994 | Baumgartner | A61F 2/442 606/247 |
| 5,429,863 | A | * | 7/1995 | McMillin | A61F 2/30965 428/370 |
| 5,534,030 | A | * | 7/1996 | Navarro | A61F 2/30767 623/17.15 |
| 5,674,294 | A | * | 10/1997 | Bainville | A61F 2/442 623/17.16 |
| 5,702,450 | A | * | 12/1997 | Bisserie | A61F 2/442 623/17.16 |
| 5,749,916 | A | * | 5/1998 | Richelsoph | A61F 2/4455 606/247 |
| 6,039,762 | A | * | 3/2000 | McKay | A61F 2/44 606/247 |
| 6,136,031 | A | * | 10/2000 | Middleton | A61F 2/30744 623/17.16 |
| 6,245,108 | B1 | * | 6/2001 | Biscup | A61F 2/4455 606/246 |
| 6,315,797 | B1 | * | 11/2001 | Middleton | A61F 2/30744 623/17.16 |
| 6,395,035 | B2 | * | 5/2002 | Bresina | A61F 2/442 606/247 |
| 6,548,002 | B2 | * | 4/2003 | Gresser | A61F 2/30965 264/229 |
| 6,569,201 | B2 | * | 5/2003 | Moumene | A61F 2/447 606/247 |
| 6,758,863 | B2 | * | 7/2004 | Estes | A61F 2/442 623/17.11 |
| 7,235,102 | B2 | * | 6/2007 | Ferree | A61F 2/34 623/17.12 |
| 7,252,685 | B2 | * | 8/2007 | Bindseil | A61F 2/4455 427/2.26 |
| 7,455,674 | B2 | * | 11/2008 | Rose | A61L 17/12 264/177.17 |
| 7,601,174 | B2 | * | 10/2009 | Kelly | A61B 17/02 623/17.13 |
| 7,618,461 | B2 | * | 11/2009 | Trieu | A61F 2/441 623/17.11 |
| 7,723,395 | B2 | * | 5/2010 | Ringeisen | A61B 17/0642 521/50 |

(Continued)

OTHER PUBLICATIONS

Tensile Modulus—Modulus of Elasticity or Young's Modulus—for some common Materials. http://www.engineeringtoolbox.com/young-modulus-d_417.html.*

(Continued)

*Primary Examiner* — Lynnsy Summitt
(74) *Attorney, Agent, or Firm* — Nixon & Vanderhye P.C.

(57) ABSTRACT

The invention is directed to a spinal fusion cage for implantation between two adjacent vertebrae, wherein the total cage has, under a load, a maximum compression that is higher than 0.05% of the original height of the spinal fusion cage and the maximum compression does not change the structural integrity of the cage.

16 Claims, No Drawings

(56) References Cited

U.S. PATENT DOCUMENTS

| | | | | |
|---|---|---|---|---|
| 7,922,767 B2* | 4/2011 | Sack | A61F 2/442 | 606/279 |
| 7,993,403 B2* | 8/2011 | Foley | A61F 2/4455 | 623/17.11 |
| 8,092,533 B2* | 1/2012 | Melkent | A61B 17/7062 | 623/17.11 |
| 8,152,849 B2* | 4/2012 | Biedermann | A61B 17/7026 | 623/17.15 |
| 8,172,902 B2* | 5/2012 | Kapitan | A61F 2/442 | 623/17.14 |
| 8,197,548 B2* | 6/2012 | Sack | A61F 2/442 | 623/17.11 |
| 8,236,055 B2* | 8/2012 | Cordaro | A61F 2/442 | 623/17.11 |
| 8,277,508 B2* | 10/2012 | Trieu | A61F 2/4425 | 623/17.15 |
| 8,361,150 B2* | 1/2013 | Zhang | B32B 15/08 | 623/17.11 |
| 2002/0128714 A1* | 9/2002 | Manasas | A61F 2/442 | 623/17.15 |
| 2002/0143403 A1* | 10/2002 | Vaidyanathan | A61L 27/446 | 623/23.51 |
| 2003/0093152 A1* | 5/2003 | Pedersen | A61B 17/025 | 623/14.12 |
| 2003/0105527 A1* | 6/2003 | Bresina | A61B 17/1637 | 623/17.16 |
| 2004/0010313 A1* | 1/2004 | Aston | A61L 31/146 | 623/17.11 |
| 2004/0220672 A1* | 11/2004 | Shadduck | A61F 2/30965 | 623/17.16 |
| 2004/0230309 A1* | 11/2004 | DiMauro | A61F 2/441 | 623/17.12 |
| 2005/0015150 A1* | 1/2005 | Lee | A61F 2/442 | 623/17.12 |
| 2005/0085915 A1* | 4/2005 | Steinberg | A61B 17/1666 | 623/17.16 |
| 2005/0100578 A1* | 5/2005 | Schmid | A61F 2/28 | 424/423 |
| 2005/0119752 A1* | 6/2005 | Williams | A61F 2/442 | 623/17.16 |
| 2005/0143821 A1* | 6/2005 | Zdeblick | A61B 17/1757 | 623/17.11 |
| 2005/0154463 A1* | 7/2005 | Trieu | A61F 2/441 | 623/17.16 |
| 2005/0171611 A1* | 8/2005 | Stoy | A61F 2/441 | 623/17.16 |
| 2005/0177245 A1* | 8/2005 | Leatherbury | A61B 17/7059 | 623/23.5 |
| 2005/0222683 A1* | 10/2005 | Berry | A61F 2/442 | 623/17.13 |
| 2005/0246021 A1* | 11/2005 | Ringeisen | A61B 17/0642 | 623/17.11 |
| 2006/0106459 A1* | 5/2006 | Truckai | A61B 17/7095 | 623/17.11 |
| 2006/0111785 A1* | 5/2006 | O'Neil | A61F 2/442 | 623/17.16 |
| 2006/0241758 A1* | 10/2006 | Peterman | A61B 17/562 | 623/17.11 |
| 2006/0282166 A1* | 12/2006 | Molz | A61F 2/442 | 623/17.13 |
| 2006/0293753 A1* | 12/2006 | Thramann | A61F 2/442 | 623/17.13 |
| 2007/0027544 A1* | 2/2007 | McCord | A61F 2/447 | 623/17.11 |
| 2007/0043443 A1* | 2/2007 | Snell | A61F 2/442 | 623/17.13 |
| 2007/0050037 A1* | 3/2007 | Snell | A61F 2/442 | 623/17.16 |
| 2007/0050038 A1* | 3/2007 | Snell | A61F 2/442 | 623/17.16 |
| 2007/0150059 A1* | 6/2007 | Ruberte | A61F 2/441 | 623/17.12 |
| 2007/0150064 A1* | 6/2007 | Ruberte | A61F 2/442 | 623/17.16 |
| 2007/0185580 A1* | 8/2007 | Posel | A61F 2/4465 | 623/17.16 |
| 2007/0219638 A1* | 9/2007 | Jones | A61F 2/4081 | 623/19.11 |
| 2007/0255417 A1* | 11/2007 | Koole | A61L 27/50 | 623/17.16 |
| 2007/0276492 A1* | 11/2007 | Andrews | A61F 2/442 | 623/17.11 |
| 2007/0293948 A1* | 12/2007 | Bagga | A61F 2/4455 | 623/17.11 |
| 2008/0021462 A1* | 1/2008 | Trieu | A61L 27/34 | 623/17.11 |
| 2008/0046082 A1* | 2/2008 | Lee | A61F 2/442 | 623/17.16 |
| 2008/0077244 A1* | 3/2008 | Robinson | A61F 2/442 | 623/17.16 |
| 2008/0161920 A1* | 7/2008 | Melkent | A61B 17/7062 | 623/17.11 |
| 2008/0167686 A1* | 7/2008 | Trieu | A61F 2/442 | 606/249 |
| 2008/0183292 A1* | 7/2008 | Trieu | A61F 2/442 | 623/17.11 |
| 2008/0249627 A1* | 10/2008 | Moehlenbruck | A61F 2/442 | 623/17.16 |
| 2008/0269900 A1* | 10/2008 | Reah | A61F 2/442 | 623/17.16 |
| 2008/0288074 A1* | 11/2008 | O'Neil | A61F 2/442 | 623/17.16 |
| 2009/0012617 A1* | 1/2009 | White | A61B 17/562 | 623/17.11 |
| 2009/0012621 A1* | 1/2009 | James | A61F 2/442 | 623/17.16 |
| 2009/0012622 A1* | 1/2009 | James | A61F 2/442 | 623/17.16 |
| 2009/0030525 A1* | 1/2009 | Desrosiers | A61K 45/06 | 623/23.62 |
| 2009/0093885 A1* | 4/2009 | Levieux | A61F 2/442 | 623/17.16 |
| 2009/0118835 A1* | 5/2009 | Robinson | A61F 2/442 | 623/17.16 |
| 2009/0125112 A1* | 5/2009 | Robinson | A61F 2/442 | 623/17.16 |
| 2009/0187247 A1* | 7/2009 | Metcalf, Jr. | A61F 2/447 | 623/17.16 |
| 2009/0222098 A1* | 9/2009 | Trieu | A61F 2/442 | 623/17.16 |
| 2009/0222099 A1* | 9/2009 | Liu | A61F 2/442 | 623/17.16 |
| 2009/0234456 A1* | 9/2009 | Nycz | A61F 2/442 | 623/17.16 |
| 2009/0259314 A1* | 10/2009 | Linder-Ganz | A61F 2/3872 | 623/14.12 |
| 2009/0326657 A1* | 12/2009 | Grinberg | A61F 2/4425 | 623/17.16 |
| 2010/0280550 A1* | 11/2010 | Reo | A61B 17/7062 | 606/249 |
| 2010/0324689 A1* | 12/2010 | Obrigkeit | A61L 31/14 | 623/17.16 |
| 2011/0015743 A1* | 1/2011 | Deslauriers | A61F 2/4455 | 623/17.16 |
| 2011/0029084 A1* | 2/2011 | Milbocker | A61F 2/442 | 623/17.16 |
| 2011/0029087 A1* | 2/2011 | Haider | A61F 2/442 | 623/17.16 |
| 2011/0082553 A1* | 4/2011 | Abdou | A61B 17/025 | 623/17.16 |
| 2011/0093076 A1* | 4/2011 | Reo | A61F 2/442 | 623/17.16 |
| 2011/0218632 A1* | 9/2011 | Reah | A61F 2/442 | 623/17.16 |
| 2012/0221107 A1* | 8/2012 | Sack | A61F 2/442 | 623/17.16 |

OTHER PUBLICATIONS

PBT http://www.matbase.com/material-categories/natural-and-synthetic-polymers/engineering-polymers/material-properties-of-polybutylene-terephthalate-pbt.html#properties.*

* cited by examiner

SPINAL FUSION CAGE

This application is the U.S. national phase of International Application No. PCT/EP/2010/052854 filed 5 Mar. 2010 which designated the U.S. and claims priority to PCT Application PCT/EP2009/052643, filed 5 Mar. 2009, and EP 09169519.7 filed 4 Sep. 2009, the entire contents of each of which are hereby incorporated by reference.

FIELD

The invention is directed to spinal fusion cages, a process for the production of spinal fusion cages and spinal fusion systems comprising the spinal fusion cages.

BACKGROUND AND SUMMARY

Spinal fusion, also known as spondylodesis or spondylosyndesis, is a surgical technique used to combine two or more vertebrae. Spinal fusion is done most commonly in the lumbar region of the spine, but it is also used to treat cervical and thoracic problems. There are two main surgical procedures of spinal fusion, which may be used in conjunction with each other:

Posterolateral fusion places a bone graft in between the vertebrae through a posterior or lateral approach. These vertebrae are then fixed in place with screws and/or wire through the pedicles of each vertebra attaching to a metal rod on each side of the vertebrae.

Interbody fusion places a bone graft between the vertebrae in the area usually occupied by the intervertebral disc. In preparation for the spinal fusion, the disc is removed entirely. A cage may be placed between the vertebrae to maintain spine alignment and disc height. The intervertebral cage may be made from either a polymeric material or titanium. The fusion then occurs between the endplates of the vertebrae.

Using both types of fusion is known as 360-degree fusion. Fusion rates are higher with interbody fusion.

The fusion process typically takes 6-12 months after surgery. During this time external bracing (orthotics) may be required.

Spinal fusion systems are known in the state of the art and are routinely used by spine surgeons to keep adjacent vertebrae in a desired position while spinal fusion takes place.

Spinal fusion systems can consist of a spinal fusion cage, which is placed between two adjacent vertebrae to facilitate spinal fusion. Spinal fusion systems can also consist of a rod or a plate that is connected to two adjacent vertebrae, to obtain fixation of the vertebrae with respect to each other, and can consist of a combination of both a spinal fusion cage and a rod or a plate. This invention is directed to spinal fusion systems comprising a spinal fusion cage alone or in combination with a rod or a plate.

Most common spinal fusion systems are made from metals, such as titanium or cobalt chrome alloys, or from a polymer that is commonly used in biomedical implants; polyetheretherketone (PEEK). These implant materials have a modulus which is much higher than that of bone and there is clinical evidence of implant subsidence and movement which is believed to be attributable to mechanical incompatibility between natural bone and the implant material. Also bone pressure necrosis does occur as a result of the presence of these metal implants.

Implants based on bone material from a donor (allograft) or from the patient itself (autograft) do have an inconsistent mechanical strength and show subsidence over time. The inconsistent properties of these implants make them generally unpredictable, challenging to reliably machine and especially prone to migration and explusion due to the difficulty of consistently machining teeth into the upper and lower implant contact surfaces.

There are disclosures of porous ceramic materials, for instance in US2005/0049706, that try to provide a spinal fusion system with mechanical properties comparable to that of bone. These implants are, however, still produced of very rigid and stiff material. These spinal fusion systems are not compressible and will still cause subsidence into the bone.

Spinal fusion cages made of porous polymeric material or a polymeric material with holes in it are described in respectively US 2005/0246021 and EP1818024. These cages are made of bioresorbable polymeric materials, like PLA, which materials have the disadvantage that the mechanical properties of the materials are not stable because of the resorption in the body. The polymeric material itself is not compressible. The purpose of using of a porous polymeric material is that the material can be compressed in a controlled manner to create various structural patterns within the material. The porous cages and the cages with the holes will be reduced in height permanently under a load. These spinal fusion cages are thus not designed to endure a load and will show (further) permanent deformation under loading conditions.

Therefore, there is still a need for a biostable spinal fusion cage which has a tensile modulus comparable to that of bone, which does not subside and provides a good stability.

These spinal fusion cages are provided for according to the present invention.

DETAILED DESCRIPTION

A biostable spinal fusion cage according to the invention is implanted between two adjacent vertebrae and the total cage has, under a load, a maximum compression that is higher than 0.05% of the original height of the spinal fusion cage and the maximum compression does not change the structural integrity of the cage.

Both the original height of the cage and the compressed height are expressed in mm. The original height of the spinal fusion cage is the shortest distance between the contact area of the spinal fusion cage with one vertebra and the other contact area of the same spinal fusion cage with the adjacent vertebra without any applied load on the spinal cage.

The compressed height is the height (in mm) of the spinal fusion cage under mechanically compressive conditions at a load equal to a stress level of 2 MPa working on the contact areas of the cage. 2 MPa is already higher than the compressive yield strength of trabecular vertraba bone in humans (Kopperman, D. L., Biomechanics 31, 601-608) and thus provides the boundary condition for undesirable subsidence of the cage into the bone.

The compressed height of the cage is reached when a load is applied to the contact area(s) of the spinal fusion cage leading to mechanical deformation of the cage. The compressed height of the cage is only reached during mechanical testing of the cage and normally not under conditions that occur in the body of a human or other mammal. The mechanical deformation does not lead to failure or permanent deformation of the cage.

The maximum compression is the difference in mm between the original height and the compressed height at a load equal to a stress level of 2 MPa working on the contact areas of the cage.

A maximum compression higher than 0.05% of the original height of the spinal fusion cage is a compression that is more than the maximum compression of the conventional materials, such as metal, ceramics or PEEK. Preferably, the maximum compression is more than 0.1% of the original height of the spinal fusion cage.

The maximum compression preferably is less than 12% of the original height of the spinal fusion cage; more preferably less than 10% of the original height of the spinal fusion cage.

The maximum compression is a measure for the deformation of the spinal fusion cage when a load is applied to the spinal fusion cage. A spinal fusion cage must be strong enough to bear the load of the human or animal body and to withstand the normal movements of the body without failure. A spinal fusion cage also must have flexibility to be able to absorb shocks of the human or animal body caused by movements, without subsidence into the bone of the vertebrae or expulsion of the cage between the vertebrae.

A higher maximum compression of a spinal fusion cage can, for instance, be achieved by design features or by the application of softer or more rubber-like materials. The spinal fusion cage can, for instance, be produced from metals, ceramics and/or polymers. Design features can be incorporated in the spinal fusion cage. These include, but are not limited to springs, coils, etc. which allow compression of the spinal fusion cage.

Preferably, the spinal fusion cage comprises a biostable polymeric material.

The polymeric material used in the spinal fusion cage can be a homopolymer, a copolymer, a block copolymer and a random copolymer. The polymer can be selected from, for instance, polyolefins, polyesters, polyamides, polyurethanes and elastomers.

Preferably, the polymeric material has a tensile modulus lower than 3500 MPa, which is a tensile modulus lower than the tensile modulus of bone.

The tensile modulus is here and hereafter defined as the modulus that is determined according to ISO 527.

The spinal fusion cage can contain one or more polymeric materials or a combination of a polymeric material with one or more other materials, such as metal or ceramics.

According to one preferred embodiment of the invention the spinal fusion cage comprises one polymeric material and a higher maximum compression of the spinal fusion cage is, for instance, achieved by foaming the polymeric material, by production of a spinal fusion cage using fused deposition modeling (FDM), by blending a certain amount of an impact modifier or a plasticizer with the polymeric material or by design features for the spinal fusion cage. Additionally, selective laser sintering (SLS) and other rapid prototyping technologies may be used to produce the spinal fusion cage.

A foam of a polymeric material can be prepared according to methods known to a person skilled in the art. Polymer materials may be converted to foamed cages or cage parts by using physical and/or chemical foaming agents. A foam can be an open-cell or a closed-cell foam.

By using FDM or SLS a predetermined three-dimensional structured cage can be prepared having a maximum compression according to the invention.

Impact modifiers are compounds that can be blended with the polymeric material to improve the impact resistance of the polymeric material. An impact modifier can for instance be a functionalized elastomeric material that is compatible with the polymer matrix. Examples of impact modifiers are elastomeric polymers (eg. Kraton®) that are used as an impact modifier in polyolefins.

Plasticizers are additives that increase the plasticity or fluidity of the material to which they are added. The most commonly used plasticizers are phthalates.

Preferably, the polymeric material in the spinal fusion cage is at least partially foamed.

According to another preferred embodiment of the invention the spinal fusion cage comprises more than one material.

For example, combinations of a metal or ceramic with a material having a much lower tensile modulus are possible.

Preferably, the spinal fusion cage comprises more than one polymeric material and
 at least one polymeric material has a tensile modulus between 0.001 and <1.0 GPa,
 at least an other polymeric material has a tensile modulus that is higher than the tensile modulus of the other polymeric material,
 the polymeric material(s) are chemically or physically connected to each other.

According to this embodiment at least two different polymeric materials are used in the spinal fusion cage. These polymeric materials possess different moduli.

The polymeric materials can be chosen from the polymeric materials described above. The polymeric materials are present as discrete parts or pieces in the spinal fusion cage. The parts or pieces are made of a polymeric material having a tensile modulus between 0.001 and <1.0 GPa or a tensile modulus that is higher than that of the other polymeric material. Preferably, the polymeric material with the higher tensile modulus has a tensile modulus between 1.0 and 20 GPa. In the parts or pieces different polymeric materials with such a tensile modulus can be mixed, but one part or piece can not contain a polymeric material with a tensile modulus between 0.001 and <1.0 GPa and a polymeric material with a tensile modulus between 1.0 and 20 GPa.

The different polymeric materials are chemically or physically connected to each other. This means that, for instance, covalent, ionic, hydrogen or van der Waals bonds can be present between the different polymeric materials. These bonds prevent the separation of the two polymeric materials that are present in the spinal fusion cage. It is also possible to connect the different polymeric materials with adhesives or other material that can bind with the different polymeric materials that form the spinal fusion cage or by mechanical constructions for connecting the different polymeric materials.

The polymeric material with the higher tensile modulus preferably is a polyester. Preferably the polyester has a tensile modulus between 1.0 and 20 GPa; more preferably a tensile modulus between 1.5 and 3 GPa.

The polyester can be a thermoplastic or a thermoset polyester. A thermosetting polyester, also known as a thermoset, is a polyester material that irreversibly cures. The curing may be done through heat (generally above 150° C.), through a chemical reaction, or irradiation.

A thermoplastic polyester, also known as thermosoftening plastic is a polymer that turns to a liquid when heated and freezes to a very glassy state when cooled sufficiently. Most thermoplastics are high-molecular-weight polymers whose chains associate through weak Van der Waals forces. Thermoplastic polyesters differ from thermosetting polymers as they can, unlike thermosetting polymers, be remelted and remoulded.

The polyester can be a homopolymer or a copolymer. Also blends of different types of polyesters can be used.

Examples of polyesters are polyethyleneterephthalate (PET), polybutyleneterephthalate (PBT), polyethylenenaphthenate (PEN) and poly(cyclohexylene-dimethyleneterephthalate) (PCT).

Preferably, the polyester is a thermoplastic polyester. Here and in the rest of the description a polycarbonate is understood to be a polyester.

Preferably, the polymeric material with a tensile modulus between 0.001 and <1.0 GPa is a thermoplastic elastomer (TPE) comprising a hard phase, and a soft phase. More preferred are TPE's with a tensile modulus of 10-1000 MPa.

Thermoplastic elastomers (TPE) are (block)copolymers or a physical blend of polymers which consist of polymeric materials with both thermoplastic and elastomeric properties. There are six generic classes of TPE's considered to exist commercially. These are styrenic block copolymers, polyolefin blends, elastomeric alloys (TPE-v or TPV), thermoplastic polyurethanes (TPU), thermoplastic copolyesters (TPC) and thermoplastic polyamides. Examples of TPE products are Styroflex (BASF), Kraton (Shell), Pellethane (Dow), Pebax (Arkema), Arnitel (DSM), Hytrel (Du Pont) Santoprene (Monsanto), Geolast (Monsanto), Sarlink (DSM), Alcryn (Du Pont) and more.

Preferably, the thermoplastic elastomers are chosen from thermoplastic copolyesters (TPC) and thermoplastic polyurethanes (TPU).

The term thermoplastic polyurethanes (TPU) encompasses a family of polymers that usually includes three principal components. These are a macroglycol, a diisocyanate and a chain extender. They are generally classified as polyurethanes in as much as the backbone thereof includes urethane groups and often also urea groups, which groups are recurring units within the polymer backbone. With particular reference to the macroglycol component of polyurethanes in general, three primary families of macroglycols are available commercially at the present time. These are the polyester glycols, the polyether glycols and the polycarbonate glycols.

Preferably, the TPE comprises a hard phase and soft phase, wherein the hard phase comprises a polymer that can be chosen from the group consisting of polyester, polyamide, polystyrene, polyacrylate and polyolefin and the soft phase comprises a polymer chosen from the group consisting of polyether, polyester, polyacrylate, polyolefin and polysiloxane.

The hard phase in the TPE comprises a rigid polymer phase with a melting temperature (Tm) or a glass transition temperature (Tg) higher than 35° C. The soft phase in the TPE comprises a flexible, amorphous polymer phase with a Tg lower than 35° C., preferably lower than 0° C. The Tm and Tg were determined on a dry sample.

Preferably, the TPE has a hard phase comprising the same polymer as the polymeric material with a tensile modulus between 1.0 and 20 GPa. For instance, a polyolefin with a tensile modulus between 1.0 and 20 GPa is combined with a TPE with a polyolefin hard phase.

The TPE, used according to the invention, comprises, for example, blends of the above-mentioned hard phase polymers with soft phase polymers and block copolymers. The hard and the soft phase can comprise one polymer type, but can also be composed of a mixture of two or more of the above-mentioned polymeric materials.

Preferably, the TPE, used according to the invention, is a block-copolymer. When the TPE is a block-copolymer, the TPE used in the spinal fusion cage comprises a polymer comprising hard blocks and soft blocks, wherein the hard blocks comprise a polymer chosen from the group consisting of polyester, polyamide, polystyrene, polyacrylate and polyolefin and the soft blocks comprise a polymer chosen from the group consisting of polyether, polyester, polyacrylate, polyolefin and polysiloxane.

Examples of TPE block copolymers are block-copolyesterester, block-copolyetherester, block-copolycarbonateester, block-copolysiloxaneester, block-copolyesteramide, block-copolymer containing polybutylene terephthalate (PBT) hard blocks and poly(oxytetramethylene) soft blocks, block-copolymer containing polystyrene hard blocks and ethylene butadiene soft blocks (SEBS), polyurethane comprising polybutylene terephthalate (PBT) hard blocks and polycarbamate soft blocks.

Also polyurethane block copolymers exist comprising hard and soft polymer blocks. Generally known polyurethane block copolymers and methods to prepare these copolymers are described in, for instance, U.S. Pat. No. 4,739,013, U.S. Pat. No. 4,810,749, U.S. Pat. No. 5,133,742 and U.S. Pat. No. 5,229,431. These polyurethane block copolymers have a hard polycarbonate phase and are biostable.

The hard blocks in the TPE consist of a rigid polymer, as described above, with a Tm or Tg higher than 35° C. In principle the different polymers as described above can be used as the hard blocks.

Also copolymers of esters, amides, styrenes, acrylates and olefins can be used as the hard polymer block as long as the Tm or Tg of the hard polymer block is higher than 35° C.

Preferably at least one phase of the TPE; i.e. the hard phase or the soft phase comprises a polyester. More preferably, the polymeric material with a tensile modulus between 0.001 and <1.0 GPa is a TPC with a polyester hard block.

It has been found that, with respect to their use in the spinal fusion cage according to the invention, in particular TPC's or TPU's with a polyester hard block have many advantages including low creep, low compression set, high dimensional stability and high resistance to moisture. Here and in the rest of the description a polycarbonate is understood to be a polyester.

In a TPC or TPU comprising a hard polycarbonate block, the hard block consists of repeating units derived from at least one alkylene glycol and at least one aromatic dicarboxylic acid or an ester thereof. The alkylene group generally contains 2-6 carbon atoms, preferably 2-4 carbon atoms. Preferable for use as the alkylene glycol are ethylene glycol, propylene glycol and in particular butylene glycol. Terephthalic acid, 2,6-naphthalenedicarboxylic acid and 4,4'-diphenyldicarboxylic acid are very suitable for use as the aromatic dicarboxylic acid. Combinations of these dicarboxylic acids, and/or other dicarboxylic acids such as isophthalic acid may also be used. Their effect is to influence the crystallisation behaviour, e.g. melting point, of the hard polyester blocks.

Most preferably, the hard block is polybutyleneterephthalate.

The soft blocks in the TPC or TPU consist of a flexible polymer, as described above, with a Tg lower than 35° C. In principle the polymers as described above can be used as the soft blocks. Also copolymers of ethers, esters, acrylates, olefins and siloxanes can be used as the soft polymer block as long as the Tg of the soft polymer block is lower than 35° C.

Preferably, the soft block comprises a polyester or a polyether; more preferably an aliphatic polyester or polyether. A particular advantage of TPC's or TPU's comprising polyester, or polyether soft blocks is that aliphatic polyesters, and polyethers feature a high chemical stability. Especially, alkylene carbonates and aliphatic polyesthers are preferred as the soft block, which result in TPC's or TPU's with particularly low moisture sensitivity and favourable adhesive properties. Preferably, the soft blocks in the TPC or TPU are derived from at least one alkylene carbonate and optionally, a polyester made up of repeating units derived from an aliphatic diol and an aliphatic dicarboxylic acid.

The alkylene carbonate can be represented by the formula

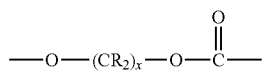

where
R=H, alkyl or aryl,
x=2-20.

Preferably, R=H and x=6 and the alkylene carbonate is therefore hexamethylene carbonate.

The aliphatic diol units are preferably derived from an alkylenediol containing 2-20 C atoms, preferably 3-15 C atoms, in the chain and an alkylenedicarboxylic acid containing 2-20 C atoms, preferably 4-15 C atoms.

More preferably, the soft block comprises a polycarbonate.

Most preferably, the TPC comprises a hard block comprising polybutyleneterephthalate and a soft block comprising polycarbonate. Optionally, this TPC is chain-extended with diisocyanate.

Examples and the preparation of block-copolyester esters are for example described in the Handbook of Thermoplastics, ed. O. Olabishi, Chapter 17, Marcel Dekker Inc., New York 1997, ISBN 0-8247-9797-3, Thermoplastic Elastomers, 2nd Ed., Chapter 8, Carl Hanser Verlag (1996), ISBN 1-56990-205-4, and the Encyclopedia of Polymer Science and Engineering, Vol. 12, pp. 75-117, and the references contained therein.

The spinal fusion cage will be implanted between two adjacent vertebrae. Thus at least one polymeric material that is present in the cage is in contact with each of these vertebrae.

Preferably, the polymeric materials with a tensile modulus between 0.001 and <1.0 GPa or a tensile modulus between 1.0 and 20 GPa are present as layers in the spinal fusion cage. The layers are oriented in such a way that the load that is borne by the spinal fusion cage is transferred to the different layers present in the cage. To state it differently; there are different layers of polymeric material present between the one and the other vertebrae.

More preferably, the polymeric materials are present as layers of material and the polymeric material with the higher tensile modulus is embedded between two layers of the polymeric material having a tensile modulus between 0.001 and <1.0 GPa.

Examples for the composition of the layers in the spinal fusion cage are polypropylene as the material with the higher tensile modulus combined with a TPV (Sarlink) as the material with the lower tensile modulus, polyamide as the material with the higher tensile modulus combined with a thermoplastic polyamide as the material with the lower tensile modulus, polyester as the material with the higher tensile modulus combined with a TPC as the material with the lower tensile modulus and a polyester as the material with the higher tensile modulus combined with a TPU as the material with the lower tensile modulus.

The spinal fusion cages can be prepared in many different ways. The parts or pieces of the polymeric material can be produced by any known method to shape such polymeric materials. Known techniques include (co-)injection molding, (co-)extrusion molding, blow molding, injection overmolding, MuCell® microcellular foam injection molding, co-extrusion of plates, or creating injection molded foams by decomposing additives like citric acid.

Other processes that can be used are rapid prototyping processes, such as selective layered sintering and fused deposition modeling.

In spinal fusion cages that contain more than one polymeric material the cages the parts or pieces made from different polymeric materials can be combined by for instance gluing, welding or molding.

Preferably, multi component molding is used for the preparation of the spinal fusion cages that contain more than one polymeric material.

Multi component molding is also called "Two-Shot" or "Multi-Shot" Injection Molding. This is a technology that combines two or more materials in a single mold. Multi component molding makes it possible to produce designs comprising hard and soft parts, or parts with different properties. There are various processes that can be used:

Multi-Shot Over-Molding is the process of molding one plastic over another in one mold. The process is very accurate since the part never leaves the mold. The adhesion of the different materials is superior as the substrate is still hot when the over-molding takes place. Good adhesion prevents separation of the spinal fusion cage parts, which may lead to a number of complications including cage migration, blood vessel and/or nerve damage from the migrated cage.

Multi-Process molding is a method of molding different parts made from different materials in the same mold. This can be especially useful when two parts are used together such as a welded assembly.

In-Mold Assembly is similar to Multi-Process molding, only utilizing mechanisms within the mold to assemble the different parts (when geometry allows) and produce an assembled unit each cycle.

Sandwich Molding, sometimes called "Co-Injection", is a process where one material is injected through the liquid melt of another material forming a core material with a skin of the other material on the outside.

The spinal fusion cages are used as a spinal fusion system alone or in combination with other cages. The cages can also be combined with one or more rods to achieve spinal fusion.

The rod can for instance be made of metal or a polymeric material.

Preferably, a rod comprises polymeric material. In this way also the rod in a spinal fusion system has a tensile modulus comparable to that of bone; which is a tensile modulus lower than 3500 MPa.

More preferably, a rod comprises at least two different polymeric materials to make the rod more flexible and allow for solid fixation into the pedicle screws.

The invention will hereafter be illustrated with reference to the following, non-limiting examples.

EXAMPLES

Materials

Arnitel® CM551 (hard phase: polybutylene terepthalate (PBT), soft phase: polycarbonate) from DSM N.V.
Arnitel® EL250 (hard phase: polybutylene terepthalate (PBT), soft phase: polytetramethyleneoxide (PTMO)) from DSM N.V.
PBT: Arnite® T06-200 from DSM N.V.

UHMWPE: Stamylan® UH MG003 from DSM N.V.
Bionate® 75 D from DSM N.V.
Bionate® 80 A from DSM N.V.
PEEK: Ketron® PEEK-1000 from Eriks Example I The purpose of the example was to compare spinal fusion cages prepared from different materials.

All cages in the experiments described below had a rectangular (18×10×6 mm³) open box configuration and wall thickness of 1.5 mm.

Cages prepared from six different types of material were tested:

a. PEEK (comparative experiment);
b. Arnitel® CM551; hereafter referred to as TPE cage.
c. a cage prepared with 2K molding comprising a PBT core of 4 mm thickness with a 1 mm layer of Arnitel® EL250 at the top and the bottom of the cage; hereafter referred to as 2Ka cage.
d. UHMWPE
e. Bionate® 75D; hereafter referred to as B 75D cage
f. a cage prepared with 2K molding comprising a core of Bionate® 75D of 3 mm thickness with a 1.5 mm layer of Bionate® 80A at the top and the bottom of the cage; hereafter referred to as 2 Kb cage.

The following experiments were done:

1. Determination of the Mechanical Cage Properties by Static Testing

Cages must have enough strength to withstand peak loads after implantation. Quasi-static loading tests determined the strength and the stiffness of the bare cage.

Experiments were performed according to ASTM2077-03. Loading speed was 13 mm/min according to the same guideline. In each experiment three cages were tested (n=3).

2. Determination of Subsidence into Bone Under Static and Dynamic Loading Regime Subsidence of the cage into the bone bed was determined according to ASTM 2267, using a polyurethane foam (grade 15, ASTM 1839) as a reproducible bone bed simulator. As incongruence between the implant and the bone bed appeared to be an important parameter for cage loading and subsidence, one foam bed was machined to have a curved surface with a radius of 28 mm. The other foam bed remained flat. First, the static strength of an open cage on the foam bed was determined for all three cage types. The foam appeared to fail at a load of some 450N. Subsequently, static loading at 70% of this static strength (i.e.: 300 N) was applied on the two polyurethane blocks and the cage in between for a period of ten minutes. Secondly, a dynamic load (sine wave) of 50-300N was applied at a frequency of 2 Hz for 100.000 cycles (app. 15 h) Comparisons were made between empty cages (worst case scenario). The number of samples was three for each type of cage material (n=3).

3. Expulsions Experiments

Expulsion testing was performed according to a test described by Goel et al., Summer Bioengineering Conference, Key Biscayne, Fla., June 2003. The expulsion test was performed on cages clamped between two flat polyurethane foam blocks (grade 15, ASTM 1839) under a pre-load of 300N and a constant speed of 0.4 mm/s. The sample number was three for all cage types.

Results

The results of the experiments are given in Table 1.

TABLE 1

| Sample type | Static test Strength (kN) | Static test Stiffness (kN/mm) | Static Sub-sidence (mm) | Dynamic Sub-sidence (mm) | Expulsion Force (N) |
|---|---|---|---|---|---|
| PEEK | 10.3 | 27.4 | 0.81 | 0.84 | 142 |
| TPE | 3.1 | 5.2 | 0.81 | 0.85 | 263 |
| 2Ka | 3.8 | 1.0 and 4.3 | 0.58 | 0.67 | 330 |
| UHMWPE | 2.8 | 8.4 | 0.98 | n.d. | 310 |
| B 75D | 5.4 | 17.3 | 0.98 | n.d. | 217 |
| 2Kb | 2.0 | 1.1 and 4.1 | 0.63 | n.d. | 423 | n.d. = not determined

All cages were strong enough to be considered sufficient for in vivo loads in animals as well as humans (equivalent to approximately 10 times body weight).

Surprisingly, the TPE, the UHMWPE and the 2Ka+b cages showed marked improvements in expulsion/migration.

Additionally, the two 2K cages showed further improvements in subsidence.

Static and dynamic subsidence experiments showed that the 2K cages performed better in that respect as well: subsidence was more than 20% less when compared to the "hard" PEEK cages. The friction of the 2K cages resulted in the highest expulsion strength.

Finally, the 2K cages showed a remarkable behavior with two ranges of stiffness; first a very low stiffness of around 1.0 kN/mm, followed by a stiffness comparable to the TPE cage. The stiffness of both the TPE, UHMWPE and 2K cages were an order of magnitude lower than of the PEEK cages; this may stimulate bone growth within the cage in an in vivo situation.

The invention claimed is:

1. A spinal fusion cage for implantation between two adjacent vertebrae, the spinal fusion cage comprising at least first and second polymeric materials present as layers, wherein a layer of the second polymeric material is embedded between two layers of the first polymeric material, and the first and second polymeric materials are chemically or physically connected to one another, and wherein the first polymeric material of the spinal fusion cage has a tensile modulus between 0.001 and <1.0 GPa, and wherein the second polymeric material of the spinal fusion cage has a tensile modulus between 1.0 and 20 GPa, and wherein the spinal fusion cage has a maximum compression that is higher than 0.05% of an original height of the spinal fusion cage, wherein the maximum compression is defined as a difference in millimeters (mm) between original and compressed heights of the spinal fusion cage at a load equal to a stress level of 2 MPA working on contact areas thereof wherein the maximum compression does not change structural integrity of the cage.

2. The spinal fusion cage according to claim 1, wherein the maximum compression is lower than 12% of the original height of the spinal fusion cage.

3. The spinal fusion cage according to claim 1, wherein at least one of the at least first and second polymeric materials comprises a biostable polymeric material.

4. The spinal fusion cage according to claim 1, wherein at least one of the at least first and second polymeric materials comprises a foamed polymeric material.

5. The spinal fusion cage according to claim 1, wherein the second polymeric material is a polyester.

6. The spinal fusion cage according to claim 5, wherein the polyester comprises a material selected from the group consisting of polyethyleneterephthalate, polybutyleneterephthalate, polyethylenenaphthenate, and poly(cyclohexylene-dimethyleneterephthalate).

7. The spinal fusion cage according to claim 6, wherein the polyester comprises polybutyleneterephthalate.

8. The spinal fusion cage according to claim 1, wherein the first polymeric material is a thermoplastic elastomer comprising a hard phase and a soft phase.

9. The spinal fusion cage according to claim 8, wherein the thermoplastic elastomer comprises a material selected from the group consisting of thermoplastic polyurethanes, thermoplastic copolyesters, and thermoplastic polyamides.

10. The spinal fusion cage according to claim 9, wherein the thermoplastic elastomer comprises thermoplastic polyurethane.

11. The spinal fusion cage according to claim 10, wherein the thermoplastic polyurethane further comprises polyester hard block.

12. The spinal fusion cage according to claim 11, wherein the polyester hard block comprises a hard polycarbonate block.

13. A process for the production of a spinal fusion cage according to claim 1, which comprises bringing together the first and second polymeric materials by multi-component molding.

14. A spinal fusion system comprising a spinal fusion cage according to claim 1.

15. The system according to claim 14, further comprising a rod of polymeric material.

16. The spinal fusion cage according to claim 1, wherein the second polymeric material comprises polycarbonate.

* * * * *